United States Patent [19]
Knudson et al.

[11] Patent Number: 5,908,029
[45] Date of Patent: Jun. 1, 1999

[54] CORONARY ARTERY BYPASS WITH REVERSE FLOW

[75] Inventors: Mark B. Knudson, Shoreview; Katherine S. Tweden, Mahtomedi, both of Minn.

[73] Assignee: HeartStent Corporation, St. Paul, Minn.

[21] Appl. No.: 08/915,539

[22] Filed: Aug. 15, 1997

[51] Int. Cl.$^6$ .................................................. A61B 19/00
[52] U.S. Cl. ............................................ 128/898; 604/49
[58] Field of Search .............................. 128/898; 604/49, 604/96; 606/194; 623/2, 3, 66

[56] References Cited

U.S. PATENT DOCUMENTS

| | | |
|---|---|---|
| 4,546,499 | 10/1985 | Possis et al. . |
| 4,562,597 | 1/1986 | Possis et al. . |
| 4,581,017 | 4/1986 | Sahota . |
| 4,862,886 | 9/1989 | Clarke et al. . |
| 4,995,857 | 2/1991 | Arnold . |
| 5,071,406 | 12/1991 | Jang . |
| 5,106,386 | 4/1992 | Isner et al. ................................ 606/15 |
| 5,209,731 | 5/1993 | Sterman et al. . |
| 5,254,097 | 10/1993 | Schock et al. . |
| 5,256,150 | 10/1993 | Quiachon et al. . |
| 5,275,622 | 1/1994 | Lazarus et al. . |
| 5,287,861 | 2/1994 | Wilk . |
| 5,370,685 | 12/1994 | Stevens . |
| 5,395,349 | 3/1995 | Quiachon et al. . |
| 5,409,019 | 4/1995 | Wilk . |
| 5,425,705 | 6/1995 | Evard et al. . |
| 5,429,144 | 7/1995 | Wilk . |
| 5,452,733 | 9/1995 | Sterman et al. . |
| 5,458,574 | 10/1995 | Machold et al. . |
| 5,484,418 | 1/1996 | Quiachon et al. . |
| 5,489,295 | 2/1996 | Piplani et al. . |
| 5,501,698 | 3/1996 | Roth et al. . |
| 5,505,725 | 4/1996 | Samson et al. . |
| 5,655,548 | 8/1997 | Nelson et al. ........................... 128/898 |
| 5,662,124 | 9/1997 | Wilk ........................................ 128/898 |

FOREIGN PATENT DOCUMENTS

| | | |
|---|---|---|
| 0 515 867 A2 | 12/1992 | European Pat. Off. . |
| WO 97/13463 | 4/1997 | WIPO . |
| WO 97/13471 | 4/1997 | WIPO . |

OTHER PUBLICATIONS

Alfred Goldman, M.D., et al., Experimental Methods for Producing a Collateral Circulation to the Heart Directly from the Left Ventricle, 31 J. Thoracic Surg. 364–374 (Mar. 1956).

Massimo, M.D., et al., Myocardial Revascularization by a New Method of Carrying Blood Directly From the Left Ventricular Cavity into the Coronary Circulation, 34 J. Thoracic Surg. 257–264 (Aug. 1957).

Mirhoseini, M.D., et al., Myocardial Revascularization by Laser: A Clinical Report, 3 Lasers in Surgery and Medicine 241–245 (1983).

Ian Munro, et al., The Possibility of Myocardial Revascularization by Creation of a Left Ventriculocoronary Artery Fistula, 58 J. Thoracic & Cardiovascular Surgery 25–32 (Jul. 1969).

Roque Pifarre, M.D., et al. Myocardial Revascularization from the Left Ventricle: A Physiologic Impossibility, 19 Surgical Forum 157–159 (1968).

Lee et al. "Effects of Laser Irradiation Delivered by Flexible Fiberoptic System on the Left Ventricular Internal Myocardium" Am Heart J 106(3):587–590, Sep. 1983.

*Primary Examiner*—David H. Willse
*Assistant Examiner*—Kelly O'Hara
*Attorney, Agent, or Firm*—Merchant, Gould, Smith, Edell, Welter & Schmidt, P.A.

[57] ABSTRACT

An obstructed coronary artery is bypassed by forming a first blood flow path from a left ventricle of the heart to a coronary vein associated with the obstructed coronary artery. A second blood flow path is formed form the obstructed coronary artery to the right ventricle for blood to flow from the left ventricle through the coronary vein to the myocardium and subsequently through the coronary artery to the right ventricle in a blood flow direction opposite a normal blood flow direction in the coronary artery and coronary vein.

7 Claims, 3 Drawing Sheets

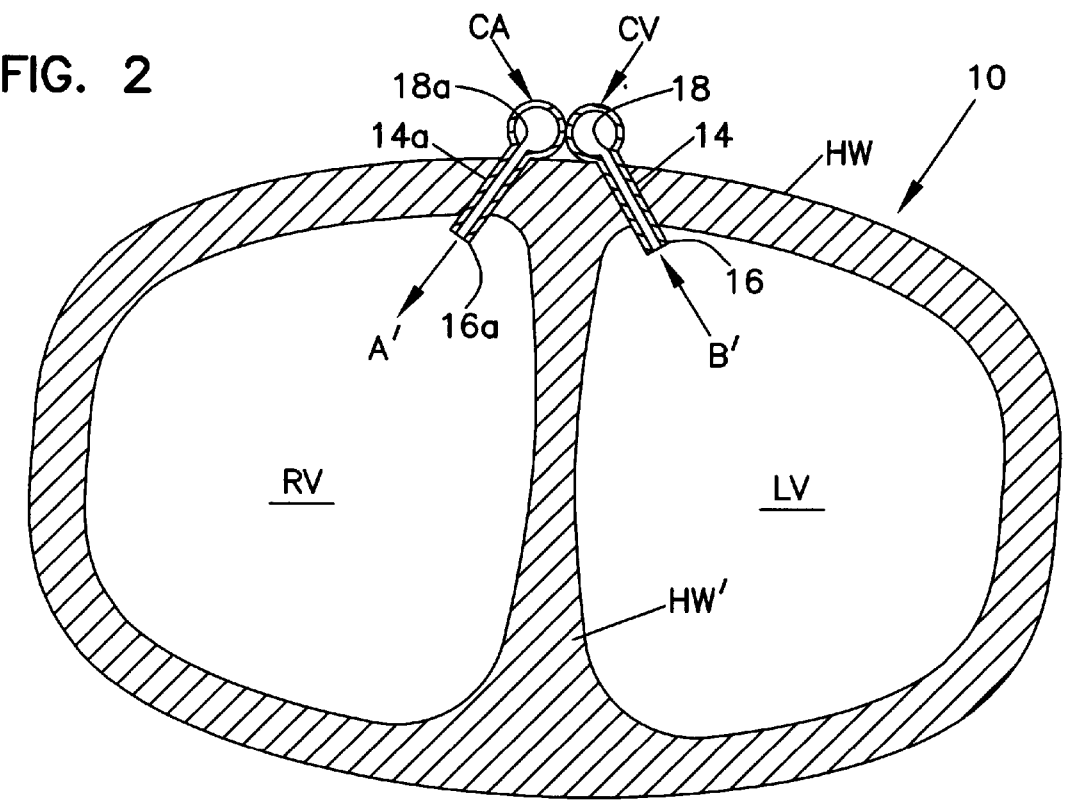
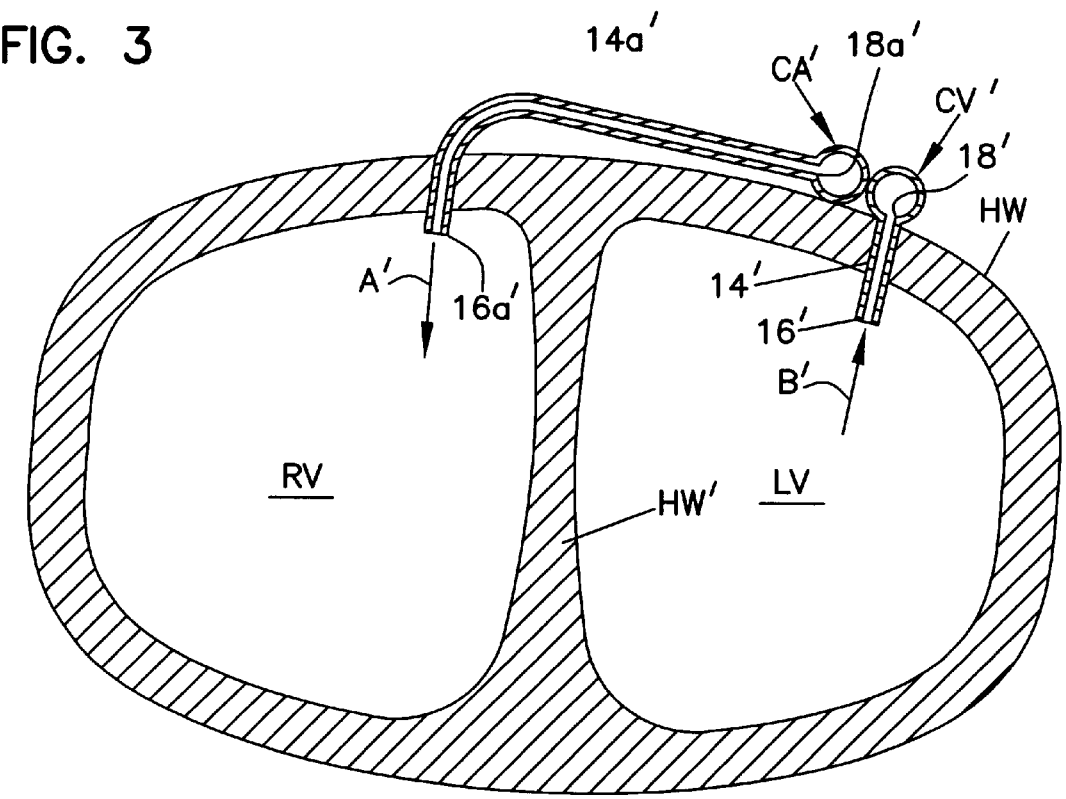

CORONARY ARTERY BYPASS WITH REVERSE FLOW

BACKGROUND OF THE INVENTION

1. Field of the Invention

This invention pertains to a method and apparatus for performing a coronary artery bypass procedure. More particularly, the present invention reverses flow in a portion of a coronary artery and a coronary vein to direct flow from an oxygenated chamber of the heart through the vein in a direction opposite normal flow and from the myocardium through the artery in a direction opposite normal flow and into a reduced pressure chamber of the heart.

2. Description of the Prior Art

Coronary artery disease is the leading cause of premature death in industrialized societies. Numerous techniques have been developed for bypassing an obstructed or diseased coronary artery. Angioplasty attempts to expand an occluded site. Commonly, a balloon-equipped catheter is used to expand an occluded site. A stent may be placed at the expanded site for the purpose of preventing reblockage. Coronary artery bypass grafting uses a harvested blood vessel from the patient to graft a bypass from the aorta to the occluded artery. Such prior art procedures have numerous problems including restenosis of angioplasty treated vessels. Grafting techniques are highly traumatic and present other problems.

New methods have been proposed as alternatives to traditional angioplasty and bypass grafting. These methods include providing a direct blood flow path from the left ventricle directly through the heart wall to the coronary artery and are described in U.S. Pat. Nos. 5,429,144, dated Jul. 4, 1995; 5,287,861, dated Feb. 2, 1994; and 5,409,019, dated Apr. 25, 1995 (all to Wilk). All of these techniques include providing a stent in the heart wall to define a direct flow path from the left ventricle of the heart to the coronary artery. The stent is closed during either diastole or systole to block return flow of blood from the coronary artery during the heart's cycle. For example, the '861 patent teaches a stent which collapses to a closed state in response to heart muscle contraction during systole. The '019 patent (particularly FIGS. 7A and 7B) teaches a rigid stent (i.e., open during systole) with a one-way valve which closes during diastole to block return flow of blood from the coronary artery. Such techniques for interruption of blood flow during either diastole or systole are undesirable since such interruption can result in areas of stagnant or turbulent blood flow. Such areas of stagnation can result in clot formation which can result in occlusion or thrombi breaking loose. Providing direct blood flow from the left ventricle to the coronary artery has been criticized. For example, Munro et al, "The Possibility Of Myocardial Revascularization By Creation of a Left Ventricle Coronary Artery Fistula", 58 *Journal Thoracic and Cardiovascular Surgery*, pgs. 25–32 (1969) shows such a flow path in FIG. 1. Noting a fallen coronary artery flow and other adverse consequences, the authors concluded "that operations designed to revascularize the myocardium direct from the cavity of the left ventricle make the myocardium ischemic and are unlikely to succeed." id at pg. 31.

In addition to the foregoing, techniques have been developed to directly revascularize the myocardium. For example, U.S. Pat. No. 5,429,144 to Wilk (FIGS. 10–12) teaches passing a stent from either the coronary artery or the left ventricle directly into but not through the myocardium for direct revascularization of the myocardium. However, these techniques are unsuitable. For example, Roque Pifarre, M.D. et al, in "Myocardial Revascularization From the Left Ventricle: a Physiological Impossibility", 19 *Surgical Forum*, 157–159 (1968), concluded that blood flow from the ventricular lumen to the myocardium to artificially create channels is a physiologic impossibility due to pressure differentials. Also, supplying a flow of blood to the myocardium without adequate drainage of blood from the myocardium can result in heart swelling and edema.

SUMMARY OF THE INVENTION

According to the present invention, a method and apparatus are provided for bypassing an obstructed coronary artery. A first blood flow path is formed from a first chamber of the heart containing oxygenated blood. The first blood flow path extends to a coronary vein associated with an obstructed coronary artery. A second blood flow path is formed from the coronary artery to a second chamber of the heart where the second chamber has a pressure less than a pressure of the first chamber. Blood flows within the vein from the first chamber to the myocardium in a direction opposite to normal vein flow direction. The blood further flows within the coronary artery from the myocardium to the second chamber in a direction opposite to normal arterial flow direction.

BRIEF DESCRIPTION OF THE DRAWINGS

FIG. 2 is a side section view of the heart taken along line 2—2 of FIG. 1;

FIG. 3 is the view of FIG. 2 showing revascularization utilizing different coronary arteries and coronary veins than those utilized in FIG. 2.

DESCRIPTION OF THE PREFERRED EMBODIMENT

With reference now to the various drawing figures in which identical elements are numbered identically throughout, a description of the preferred embodiment of the present invention will now be provided.

Figure 1:
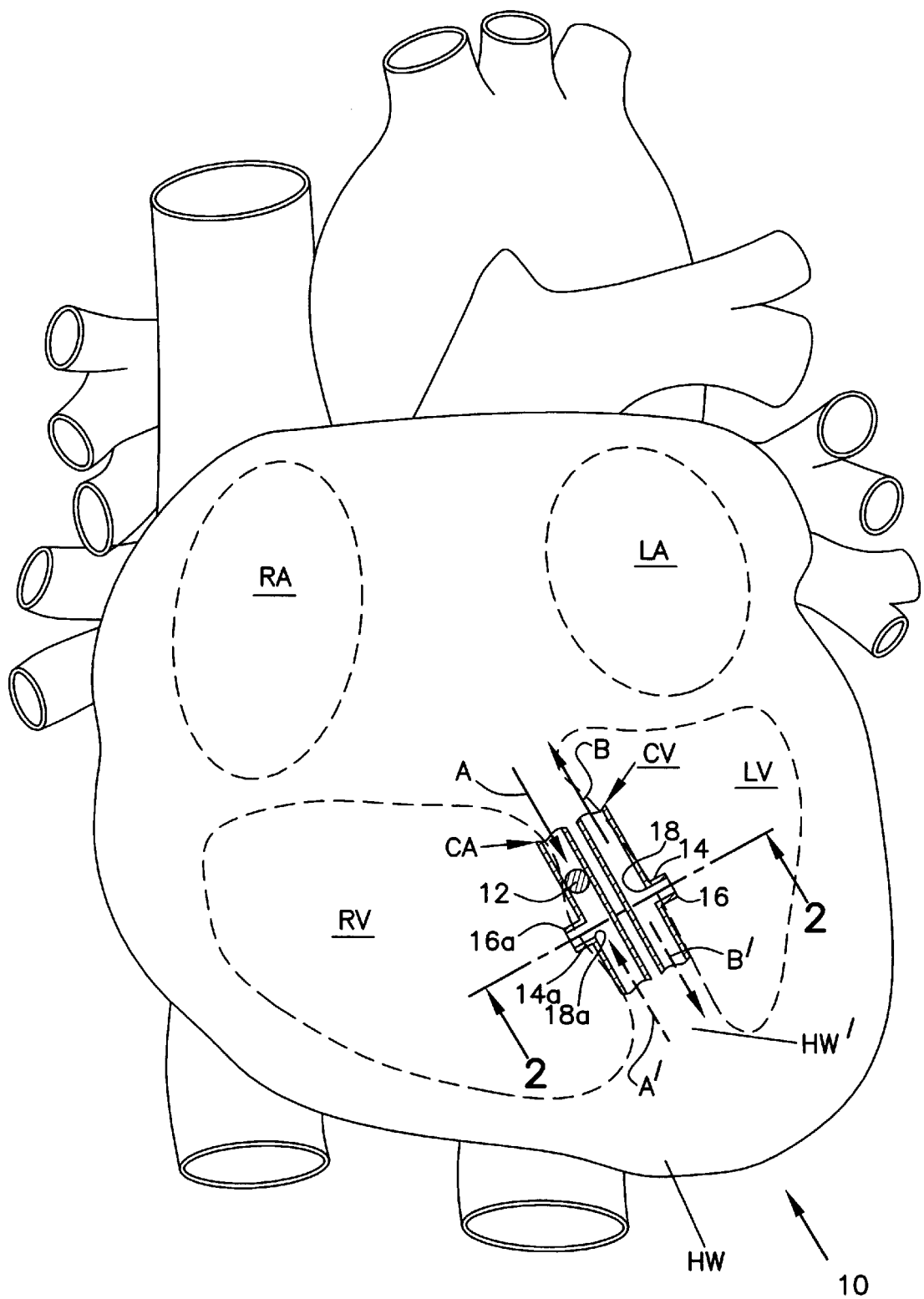
FIG. 1 is a side elevation schematic view of a heart illustrating, in phantom lines, positions of left and right atriums and left and right ventricles as well as showing partial sectional views of coronary artery and an associated coronary vein which are connected by artificial blood flow paths directly to the right ventricle and left ventricle, respectively.

With initial reference to FIGS. 1 and 2, a heart 10 is schematically shown and includes an exterior heart wall HW and having interior walls HW' with the walls HW, HW' cooperating to define interior chambers including a right atrium RA, a left atrium LA, a right ventricle RV and a left ventricle LV. Internal heart valves are not shown for ease of illustration.

A plurality of coronary arteries CA and coronary veins CV are disposed on the exterior of the heart wall HW. Commonly, coronary arteries and coronary veins are disposed on the heart wall in parallel alignment. The coronary arteries provide oxygenated blood to the myocardium of the heart wall. From the myocardium, blood flow returns through the coronary vein CV. The coronary artery CA has an associated coronary vein CV such that the portion of the myocardium supplied by the coronary artery CA is drained by the coronary vein CV.

Normally, blood from the right atrium flows into the right ventricle and is directed to the lungs for oxygenation. The oxygenated blood flows to the left atrium and subsequently to the left ventricle for distribution throughout the body. From the left ventricle, the blood flows through the aorta (not shown) and is passed through the coronary arteries flowing in the direction of arrow A representing a normal arterial blood flow direction. After flowing through the myocardium of the heart, the blood returns through the vein flowing in a normal vein flow direction illustrated by the arrow B for return to the right atrium and a repeat of the aforementioned cycle.

From time to time, the coronary artery may be occluded illustrated by the occlusion 12 in FIG. 1 such that blood flow through the coronary artery CA is impeded or blocked preventing oxygenated blood from reaching the myocardium served by the coronary artery CA. Such a condition can result in an infarction and other serious complications to the patient.

The present invention uses first and second blood flow conduits, 14, 14a, respectively. The first blood flow conduit 14 has a first end 16 in blood flow communication within the left ventricle LV. The second end 18 of the first conduit 14 is positioned in blood flow communication with the interior of the coronary vein CV. Similarly, the second blood flow conduit 14a has a first end 16a positioned in blood flow communication with the right ventricle RV and a second end 18a positioned within the interior of the coronary artery CA. The first conduit 14 defines a first blood flow path from the left ventricle LV into the coronary vein CV. The second conduit 14a defines a second blood flow path from the coronary artery CA into the right ventricle RV. The second end 18a of the second conduit 14a is positioned within the coronary artery CA at a position downstream of the obstruction 12 relative to the normal arterial flow direction A.

With the structure thus described, it will be noted that the right ventricle is commonly at a lower pressure than the left ventricle. Oxygenated blood flows from the left ventricle LV into the coronary vein CV and flows in a direction B' opposite the normal flow direction B, such that the oxygenated blood flowing in the direction B' flows to the myocardium to provide oxygenated blood to the myocardium. Blood from the myocardium then flows into the coronary artery CA in the direction of arrow A' which is opposite the direction of the normal arterial blood flow direction A. The blood then flows through the conduit 14a into the right ventricle RV where it is then passed to the lungs for reoxygenation.

Through the use of the conduits 14, 14a, the direction of blood flow within the coronary artery CA and coronary vein CV is reversed from the normal flow direction so that oxygenated blood flows from the vein CV to the myocardium and flows through the coronary arteries CA to be reoxygenated. By draining blood from the myocardium through the coronary artery CA, build up of blood within the myocardium can be avoided reducing edema. Further, oxygenated blood is provided to the myocardium at all times reducing risk of infarction.

Figure 4:
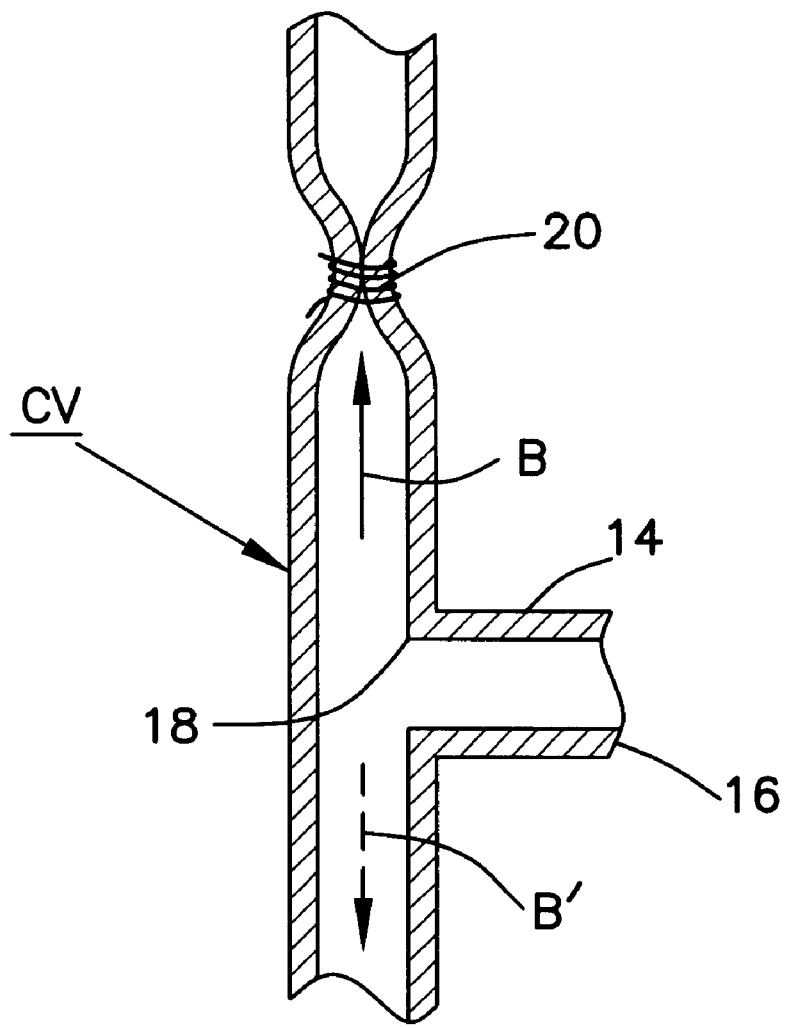
FIG. 4 is an alternative embodiment of FIG. 1 showing artificial obstruction of the coronary vein.

FIG. 4 shows an alternative embodiment to FIG. 1 where the coronary vein CV is artificially occluded upstream (relative to the normal vein flow direction B) of the second end 18 of the conduit 14. The occlusion of the coronary vein CV can be made by sutures 20 to close the coronary vein CV upstream of the conduit 14. The addition of the artificial occlusion by reason of the sutures 20 ensures that all blood flow through the conduit 14 flows in the reverse direction B' with distribution to the myocardium.

FIG. 2 illustrates the present invention where the coronary artery which is occluded is part of a coronary artery CA and coronary vein CV pair residing in alignment with an interior dividing wall HW' which separates the right ventricle RV from the left ventricle LV. In such an application, the conduits 14, 14a are rigid tubes sized to extend from the lower wall of the coronary artery CA, and coronary vein CV, and extend into the right ventricle RV and left ventricle LV to protrude within the interior of the right ventricle RV and left ventricle LV by a distance of about 1–3 mm. The tubes 14, 14a may be made of any rigid material such as metal, ceramic or polymers which are sufficiently rigid to resist contractions resulting from the heart wall HW during systole such that the tubes 14, 14a remain open to blood flow during both systole and diastole.

FIG. 3 illustrates an alternative application where the coronary artery CA' and coronary vein CV' are disposed away from the interior dividing wall HW'. In such an application, the first conduit 14' is sized to pass through the heart wall HW into the left ventricle LV with a first end 16' of the conduit 14' disposed within the interior of the left ventricle LV and with a second end 18' disposed within the coronary vein CV'. The entire length of the conduit 14' passes through the heart wall. In order to provide a conduit 14a' from the coronary artery CA' to the right ventricle RV, the second conduit 14a' has its first end 16a' in communication with the right ventricle RV and a second end 18a' in communication with the coronary artery CA'. A portion of the conduit 14a' passes through the heart wall HW with a remainder of the conduit 14a' disposed in overlying relation to the heart wall HW and with the second end 18a' entering the coronary artery CA' through the side of the coronary artery CA' rather than through the floor of the coronary artery CA' as was illustrated with reference to FIG. 2.

In the embodiments shown, the coronary arteries CA, CA' are shown with conduits 14a, 14a' with their first ends 16a, 16a' in communication with the right ventricle RV. Alternatively, the right ends 16a, 16a' could be provided in blood flow communication with the right atrium RA which is at a lower pressure than the left ventricle LV.

As further alternatives to the above, the conduits 14a, 14a' can connect the coronary artery CA, CA' to the right atrium RA, left atrium LA or the vena cava. Also, multiple second conduits 14a, 14a' can be used to increase drainage.

Having described the present invention and the preferred embodiment, modifications and equivalents of the disclosed concepts may occur to one of ordinary skill in the art. It is intended that such modifications and equivalents shall be included within the scope of the claims which are appended hereto.

What is claimed is:

1. A method for bypassing an obstructed coronary artery having an arterial blood flow direction flowing toward a myocardium of a heart and having an associated coronary vein having a venal blood flow direction flowing away from said myocardium, said heart including a plurality of chambers including a right atrium, a right ventricle, a left atrium and a left ventricle, said method comprising:

selecting a first chamber of said plurality of chambers with said first chamber selected to be one of said plurality containing oxygenated blood;

forming a first blood flow path from the first chamber of said heart to said coronary vein;

selecting a second chamber of said plurality of chambers with said second chamber selected to be one of said plurality having a pressure less than a pressure of said first chamber;

forming a second blood flow path from said coronary artery to the second chamber;

whereby said oxygenated blood from said first chamber enters said vein through said first blood path and flows within said vein from said first chamber to said myocardium in a direction opposite to said venal blood flow direction, and whereby said blood flows within said coronary artery from said myocardium to said second chamber in a direction opposite to said arterial blood flow direction and enters said second chamber through said second blood flow path.

2. A method according to claim 1 wherein said first chamber is a left ventricle of said heart.

3. A method according to claim 2 wherein said second chamber is a right ventricle of said heart.

4. A method according to claim 1 further comprising positioning said second blood flow path to enter said coronary artery at a location between an obstruction in said coronary artery and said myocardium served by said coronary artery.

5. A method according to claim 1 further comprising obstructing said coronary vein at a location downstream, relative to said venal blood flow direction, of a location of entry of said first blood flow path into said coronary vein.

6. A method according to claim 1 wherein said first blood flow path is maintained open during both diastole and systole.

7. A method according to claim 1 wherein said second blood flow path is maintained open during both diastole and systole.

* * * * *